United States Patent
Merkel et al.

(10) Patent No.: US 9,975,084 B2
(45) Date of Patent: *May 22, 2018

(54) FLUID SEPARATION PROCESSES USING MEMBRANES BASED ON FLUORINATED AND PERFLUORINATED POLYMERS

(71) Applicants: Membrane Technology and Research, Inc., Newark, CA (US); New York University, New York, NY (US)

(72) Inventors: Timothy C Merkel, San Jose, CA (US); Hao Zhang, Fremont, CA (US); Zhenjie He, Fremont, CA (US); Johannes G Wijmans, Menlo Park, CA (US); Yoshiyuki Okamoto, Brooklyn, NY (US)

(73) Assignees: Membrane Technology and Research, Inc., Newark, CA (US); New York University, New York, NY (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/608,399

(22) Filed: May 30, 2017

(65) Prior Publication Data

US 2017/0259204 A1    Sep. 14, 2017

Related U.S. Application Data

(63) Continuation-in-part of application No. 15/474,928, filed on Mar. 30, 2017, which is a continuation of application No. 15/141,303, filed on Apr. 28, 2016, now Pat. No. 9,636,632, which is a continuation-in-part of application No. 14/921,382, filed on Oct. 23, 2015, now Pat. No. 9,643,124, which is a continuation-in-part of application No. 14/330,714, filed on Jul. 14, 2014, now Pat. No. 9,403,120, which is a continuation of application No. 14/184,308, filed on Feb. 19, 2014, now Pat. No. 8,828,121.

(60) Provisional application No. 62/154,408, filed on Apr. 29, 2015, provisional application No. 62/068,176, filed on Oct. 24, 2014.

(51) Int. Cl.
| | | |
|---|---|---|
| B01D 53/22 | (2006.01) |
| B01D 71/32 | (2006.01) |
| B01D 71/38 | (2006.01) |
| B01D 61/36 | (2006.01) |
| C10L 3/10 | (2006.01) |
| B01D 53/28 | (2006.01) |
| C01B 21/04 | (2006.01) |
| C01B 23/00 | (2006.01) |
| C01B 3/50 | (2006.01) |
| C07C 7/144 | (2006.01) |

(52) U.S. Cl.
CPC ........... *B01D 53/228* (2013.01); *B01D 53/28* (2013.01); *B01D 61/36* (2013.01); *B01D 61/362* (2013.01); *B01D 71/32* (2013.01); *B01D 71/38* (2013.01); *C01B 3/503* (2013.01); *C01B 21/0444* (2013.01); *C01B 23/0047* (2013.01); *C07C 7/144* (2013.01); *C10L 3/104* (2013.01); *B01D 2256/24* (2013.01); *B01D 2256/245* (2013.01); *B01D 2257/102* (2013.01); *B01D 2257/108* (2013.01); *B01D 2257/11* (2013.01); *B01D 2257/502* (2013.01); *B01D 2257/504* (2013.01); *B01D 2257/7025* (2013.01); *B01D 2325/04* (2013.01); *C01B 2203/0405* (2013.01); *C01B 2203/048* (2013.01); *C01B 2210/007* (2013.01); *C01B 2210/0012* (2013.01); *C01B 2210/0031* (2013.01); *Y02C 10/10* (2013.01); *Y02P 20/152* (2015.11)

(58) Field of Classification Search
CPC ...... B01D 53/22; B01D 53/228; B01D 61/00; B01D 61/02; B01D 61/36; B01D 71/06; B01D 71/32; B01D 2256/245; B01D 2257/102; B01D 2257/108; B01D 2257/11; B01D 2257/504; B01D 61/362
See application file for complete search history.

(56) References Cited

U.S. PATENT DOCUMENTS

| | | |
|---|---|---|
| 3,133,132 A | 5/1964 | Loeb et al. |
| 3,307,330 A | 3/1967 | Niedzielski et al. |
| 3,308,107 A | 3/1967 | Selman et al. |
| 4,230,463 A | 10/1980 | Henis et al. |
| 4,243,701 A | 1/1981 | Riley et al. |

(Continued)

FOREIGN PATENT DOCUMENTS

| | | |
|---|---|---|
| JP | 4032738 B2 | 1/2008 |
| WO | WO2010080753 A1 | 7/2010 |

OTHER PUBLICATIONS

Yang, et al, "Novel Amorphous Perfluorocopolymeric System; Copolymers of Perfluoro-2-methylene-1,3-dioxolane Derivatives," Journal of Polymer Science, vol. 44, pp. 1613-1618 (2006).

(Continued)

*Primary Examiner* — Jason M Greene
(74) *Attorney, Agent, or Firm* — Timothy A. Hott; Suk H. Chow

(57) ABSTRACT

A process for separating components or a fluid mixture using membranes comprising a selective layer made from copolymers of an amorphous per fluorinated dioxolane and a fluorovinyl monomer. The resulting membranes have superior selectivity performance for certain fluid components of interest while maintaining fast permeance compared to membranes prepared using conventional perfluoropolymers, such as Teflon® AF, Hyflon® AD, and Cytop®.

10 Claims, No Drawings

(56) References Cited

U.S. PATENT DOCUMENTS

| | | | |
|---|---|---|---|
| 4,863,761 | A | 9/1989 | Puri |
| 5,051,114 | A | 9/1991 | Nemser et al. |
| 5,141,642 | A | 8/1992 | Kusuki et al. |
| 5,156,888 | A | 10/1992 | Haubs et al. |
| 5,242,636 | A | 9/1993 | Sluma et al. |
| 5,265,734 | A | 11/1993 | Linder et al. |
| 5,318,417 | A | 6/1994 | Kopp et al. |
| 5,408,020 | A | 4/1995 | Hung et al. |
| 6,361,582 | B1 | 3/2002 | Pinnau et al. |
| 6,361,583 | B1 | 3/2002 | Pinnau et al. |
| 6,544,316 | B2 | 4/2003 | Baker et al. |
| 6,572,679 | B2 | 6/2003 | Baker et al. |
| 6,572,680 | B2 | 6/2003 | Baker et al. |
| 6,579,341 | B2 | 6/2003 | Baker et al. |
| 6,592,650 | B2 | 7/2003 | Pinnau et al. |
| 7,078,470 | B2 | 7/2006 | Funaki et al. |
| 7,582,714 | B2 | 9/2009 | Okamoto et al. |
| 7,635,780 | B2 | 12/2009 | Okamoto et al. |
| 7,690,514 | B2 | 4/2010 | McKeown et al. |
| 7,754,901 | B2 | 7/2010 | Okamoto et al. |
| 8,056,732 | B2 | 11/2011 | McKeown et al. |
| 8,168,808 | B2 | 5/2012 | Okamoto et al. |
| 8,575,414 | B2 | 11/2013 | Liu et al. |
| 8,686,104 | B2 | 4/2014 | Du et al. |
| 8,828,121 | B1 | 9/2014 | He et al. |
| 9,079,138 | B2 | 7/2015 | Nemser et al. |
| 9,636,632 | B2 * | 5/2017 | Merkel ............... B01D 53/228 |
| 2004/0173529 | A1 * | 9/2004 | Da Costa ............... B01D 71/32 210/640 |
| 2011/0266220 | A1 * | 11/2011 | Campos ............ B01D 39/1692 210/640 |
| 2012/0097612 | A1 * | 4/2012 | Nemser ................. B01D 71/32 210/654 |
| 2012/0190091 | A1 | 7/2012 | Huang et al. |
| 2015/0025293 | A1 | 1/2015 | Feiring et al. |
| 2015/0031537 | A1 | 1/2015 | Dorner-Rieping et al. |
| 2015/0231555 | A1 | 8/2015 | He et al. |
| 2016/0002413 | A1 | 1/2016 | Wlassics et al. |

OTHER PUBLICATIONS

Liu, et al., Synthesis and Radical Polymerization of Perfluoro-2-methylene-1,3-dioxolanes, Macromolecules, vol. 38, pp. 9466-9478 (2005).

Koike, et al, Synthesis and Characterization of Copolymers of Perfluoro(2-methylene-4,5-dimethyl-1,3-dioxolane) and Perfluoro(2-methylene-1,3-dioxolane), Journal of Fluorine Chemistry, vol. 156, pp. 198-202 (2013).

Mikes, et al, Characterization and Properties of Semicrystalline and Amorphous Perfluoropolymer: Poly(perfluoro-2-methylene-1,3-dioxolane), Polym. Adv. Technol. vol. 22, pp. 1272-1277 (2011).

Paul and Chio, "Gas Permeation in a Dry Nafion Membrane," Industrial and Engineering Chemistry Research, Inc., vol. 27, pp. 2161-2164 (1988).

Okamoto, et al, "Synthesis and Properties of Amorphous Perfluorinated Polymers," Chemistry Today, vol. 27, pp. 46-48 (2009).

Nakagawa,T., "Industrial Applications of Membranes for Gas Separation in Japan," in Polymeric Gas Separation Membranes, Ed. D.R. Paul and Y.P. Yampol'skii, pp. 416-419. Boca Raton, CRC Press (1994).

Liu,et al., "Free-Radical Polymerization of Dioxolane and Dioxane Derivatives: Effect of Fluorine Substituents on the Ring Opening Polymerization", Journal of Polymer Science Part A: Polymer Chemistry, vol. 42, pp. 5180-5188 (2004).

Okamoto, et al. "New Perfluoro-Dioxolane-Based Membranes for Gas Separations", Journal of Membrane Science, vol. 471, pp. 412-419 (2014).

Ezhov, "Permeability of Fluorine and Some Other Fluorine-Containing Gases Through Nonporous Fluorine-Stable Copolymers," Atomic Energy, vol. 110, No. 3, pp. 207-211 (2011).

Ezhov, "Investigation of Permeability of Fluorine and Certain Fluorinated Gases Through Nonporous Fluorine-Resistant Polymers," Petroleum Chemistry, vol. 45, No. 8 pp. 608-611 (2014).

Mikes, et al, "Synthesis and Characterization of Perfluoro-3-methylene-2,4-dioxabicyclo[3,3,0] octane: Homo- and Copolymerization with Fluorovinyl Monomers," Journal of Polymer Science: Part A: Polymer Chemistry, vol. 47 pp. 6571-6578 (2009).

Boschet, et al, "(Co)polymers of Chlorotrifluoroethylene: Synthesis, Properties, and Applications," Chem. Rev. vol. 114 No. 2, pp. 927-980, paragraph 3.2.13, (2013).

Okamoto, et al., "Amorphous Polymers," in Handbook of Fluoropolymer Science and Technology, First Edition, John Wlley and Sons, (2014).

Teng, "Overview of the Development of the Fluoropolymer Industry," Appl. Sci., vol. 2, pp. 496-412 (2012).

Annex to form PCT/ISA/206, Communication Relating to the Results of the Partial International Search for PCT/US2016/029817, dated Jul. 27, 2016.

* cited by examiner

FLUID SEPARATION PROCESSES USING MEMBRANES BASED ON FLUORINATED AND PERFLUORINATED POLYMERS

CROSS-REFERENCE TO RELATED APPLICATIONS

This application is a continuation-in-part of U.S. Ser. No. 15/474,928, filed on Mar. 30, 2017, which is a continuation of U.S. Ser. No. 15/141,303, filed on Apr. 28, 2016, and issued as U.S. Pat. No. 9,636,632 on May 2, 2017, which claims the benefit of U.S. Provisional Patent Application No. 62/154,408, filed on Apr. 29, 2015, and is a continuation-in-part of U.S. Ser. No. 14/921,382, filed on Oct. 23, 2015, and issued as U.S. Pat. No. 9,643,124 on May 9, 2017, which claims the benefit of U.S. Provisional Patent Application No. 62/068,176, filed on Oct. 24, 2014, and is a continuation-in-part of U.S. Ser. No. 14/330,714, filed on Jul. 14, 2014 and issued as U.S. Pat. No 9,403,120 on Aug. 2, 2016, which is a continuation of Ser. No. 14/184,308, filed on Feb. 19, 2014 and issued as U.S. Pat. No. 8,828,121 on Sep. 9, 2014, all of which are hereby incorporated by reference in their entireties.

STATEMENT OF GOVERNMENTAL SUPPORT

The invention was made with Government support under Grant No. IIP-1449053 awarded by the National Science Foundation. The Government has certain rights in this invention,

FIELD OF THE INVENTION

The invention relates to membrane-based fluid separation processes. In particular, the invention relates to fluid separation processes using copolymer membranes having, a selective layer comprising a perfluorinated dioxolane monomer and a fluorovinyl monomer.

BACKGROUND OF THE INVENTION

Presented below is background information on certain aspects of the present invention as they may relate to technical features referred to in the detailed description, but not necessarily described in detail. The discussion below should not be construed as an admission as to the relevance of the information to the claimed invention or the prior art effect of the material described.

The search for a membrane for use in fluid separation applications that combines high selectivity with high flux continues. Current perfluoropolymer membranes, such as those made from Hyflon® AD (Solvay), Teflon® AF (Du Pont), Cytop® (Asahi Glass), and variants thereof, have excellent chemical resistance and stability. We reported earlier, in U.S. Pat. No, 6,361,583, membranes that are made from glassy polymers or copolymers, including Hyflon® AD, and arc characterized by having repeating units of a fluorinated, cyclic structure. In general, the ring structures in these materials frustrate polymer chain packing yielding amorphous polymers with relatively high fluid permeability. These developed membranes are also more resistant to plasticization by hydrocarbons than prior art membranes and are able to recover from accidental exposure to liquid hydrocarbons.

It is known that copolymerization of fluorinated cyclic monomers with tetrafluoroethylene (TFE) enhances the chemical resistance and physical rigidity of membranes. TFE is also known to improve processability and has the effect of lowering fluid permeability and increasing size selectivity in Hyflon® AD and Teflon® AF. Therefore, combinations of TFE with other monomer units, in particular perfluorinated dioxoles, such as in Teflon® AF and Hyflon® AD, that result in overall amorphous, yet rigid, highly fluorinated, copolymers are useful for industrial membrane applications. However, a drawback to these membranes is that their selectivities are relatively low for a number of separations of interest, including $H_2/CH_4$, $He/CH_4$, $CO_2/CH_4$, and $N_2/CH_4$.

Other than the commercially available perfluoropolymers, there is very limited fluid transport data available for fully fluorinated polymers. Paul and Chio, "Gas permeation in a dry Nation membrane," Industrial & Engineering Chemistry Research, 27, 2161-2164 (1988), examined gas transport in dry Nation® (an ionic copolymer of TFE and sulfonated perfluorovinyl ether) and found relatively high permeabilities and selectivities for several gas pairs ($He/CH_4$, $He/H_2$, and $N_2/CH_4$) compared to conventional hydrocarbon-based polymers considered for membrane applications, Nafion® and related ionic materials are used to make ion exchange membranes for electrochemical cells and the like. Because of their high cost and need for carefully controlled operating conditions, such as adjusting the relative humidity of the feed gas to prevent polymer swelling and loss of performance, these ionic membranes are not suitable for industrial gas separations, U.S. Pat. No. 5,051,114, to DuPont, discloses the testing of poly-[perfluoro-2-methylene-4-methyl-1,3-dioxolane] for use in a membrane for gas separation. The results indicated that this material exhibited gas permeabilities 2.5 to 40 times lower as compared to dipolymer membranes of perfluoro-2,2-dimethyl-1,3-dioxole and TFE, but had higher selectivities. Also disclosed are copolymers of perfluoro-2,2-dimethyl-1,3-dioxole and either tetrafluoroethylene, perfluoromethyl vinyl ether, vinylidene fluoride, or chlorotrifluoroethylene.

Recently, there have been reports of new non-ionic amorphous perfluoropolymers. U.S. Pat. Nos. 7,582,714; 7,635, 780; 7,754,901; and 8,168,808, all to Yoshiyuki Okamoto, disclose compositions and processes for making dioxolane derivatives.

Yana et al., "Novel Amorphous Perfluorocopolymeric System: Copolymers of Perfluoro-2-methylene-1,3-dioxolane Derivatives," Journal of Polymer Science: Part A: Polymer Chemistry, Vol. 44, 1613-1618 (2006), and Okamoto et al., "Synthesis and properties of amorphous perfluorinated polymers," Chemistry Today, vol. 27, n. 4, pp. 46-48 (July-August 2009), disclose the copolymerization of two dioxolane derivatives, perfluorotetrahydro-2-methylene-furo[3,4,-d][1,3]dioxolane and perfluoro-2-methylene-4-methoxymethyl-1,3-dioxolane. The copolymers were found to be thermally stable, have low refractive indices, and high optical transparency from UV to near-infrared, making them ideal candidates for use in optical and electrical materials.

Liu et al., "Free-Radical Polymerization of Dioxolane and Dioxane Derivatives: Effect of Fluorine Substituents on the Ring Opening Polymerization," Journal of Polymer Science; Part A: Polymer Chemistry, Vol. 42, 5180-5188 (2004), discloses the synthesis of partially-and fully-fluorinated dioxolane and dioxane monomers that may be used in materials for optical fiber applications.

Mikes et al., "Synthesis and Characterization of Perfluoro-3-methylene-2,4,-dioxabicyclo[3,3,0]octane: Homo- and Copolymerization with Fluorovinyl Monomers," J Polym Sci Part A: Polym Chem, 47: 6571-6578 (2009), discloses copolymers of perfluoro-3-methylene-2,3-dioxabicyclo-[3,3,0]octane with chlorotrifluoroethylene (CTFE), perfluoropropyl vinyl ether, perfluoromethyl vinyl ether, and vinylidene fluoride for use in a variety of applications.

Boshet and Ameduri "(Co)polymers of Chlorotrifluoroethylene: Synthesis, Properties, and Applications," Chem. Rev, 2014, 114, 927-980, discloses copolymers of chlorotrifluoroethylene and perfluoro-3-methylene-2,3-dioxabicyclo-[3,3,0]octane for use in optical fiber applications.

Paul and Yampol'ski, "Polymeric Gas Separation Membranes," CRC Press, pp. 416-419 (1994), discloses polymer membranes investigated by Asahi Glass Co. that contain a copolymer of tetrafluoroethylene and perfluoro-2-methylene-4-methyl-1,-3-dioxolane. However, no gas separation data is presented.

U.S. Pat. No. 9,079,138 to Nemser et al., discloses a method for making fluorinated polymeric membranes comprising, for example, a copolymer of perfluoro-2-methylene-4-methyl-1,3-dioxolane and a fluorovinyl monomer, which can be used for separating liquid components under nanofiltration type operating conditions. These membranes have a high transmembrane flux, which is unsuitable for gas separation:

Ezhov, "Investigation of Permeability of Fluorine and Certain Gases through Nonporous Fluorine-Resistant Polymers," Petroleum Chemistry, 2014, Vol. 54, No. 8, pp. 608-611, and "Permeability of Fluorine and Some Other Fluorine-Containing Gases Through Nonporous Fluorine-stable Copolymers," Atomic Energy, 2011, Vol. 110, No. 3, pp. 173-175, disclose the separation of certain fluorinated gases using thick films (30-100 μm) made of copolymers of vinylidene fluoride and perfluoro-2-methylene-4-methyl-1,3-dioxolane and perfluoro-2-methylene-1,3-dioxolane.

U.S. PGPUB 2012/0190091 to Huang et al. discloses a method for dehydrating organic/water solutions using a membrane having a selective layer firmed from highly fluorinated monomers, including copolymers of dioxolanes and fluorinated ethers and ethylene. However, no specific dioxolanes are disclosed.

To date, however, we are unaware of any published data reporting fluid separation performances of membranes made by copolymerizing perfluorodioxolane monomers with the fluorovinyl monomers as described herein.

SUMMARY OF THE INVENTION

The present invention relates to a process for separating components of a fluid mixture whereby the fluid mixture is passed across an improved separation membrane having a selective layer formed from a copolymer comprising of at least one perfluorodioxolane monomer and a fluorovinyl monomer.

As discussed above, membranes previously developed for fluid separation processes lack adequate selectivity for certain fluid separations, such as treatment of natural gas. To address the performance issues of these membranes, in co-owned U.S. Pat. No. 8,828,121, we previously examined the properties of certain specific dioxolane copolymers incorporating at least two perfluorinated dioxolane monomers of differing crystallinity. In particular, we discovered that copolymers of perfluorodioxolane monomers listed in Table 1, below, could be used as the selective layer in composite membranes having improved gas separation properties.

TABLE 1

Perfluorodioxolane Monomers

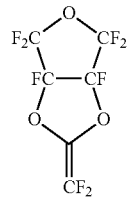

Perfluorotetrahydro-2-methylene-furo[3,4-d][1,3]-dioxolane
(Monomer A)

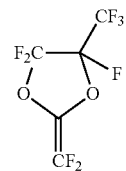

Perfluoro-2-methylene-4-methyl-1,3-dioxolane
(Monomer B)

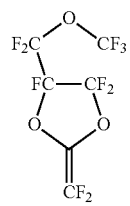

Perfluoro-2-methylene-4-methoxymethyl-1,3-dioxolane
(Monomer C)

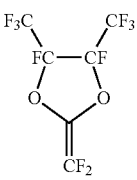

Perfluoro-2-methylene-4,5-dimethyl-1,3-dioxolane
(Monomer D)

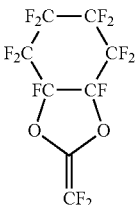

Perfluoro-3-methylene-2,4-dioxabicyclo[4,3,0]nonane
(Monomer E)

TABLE 1-continued

Perfluorodioxolane Monomers

Perfluoro-3-methylene-2,4-dioxabicyclo-
[3,3,0] octane
(Monomer F)

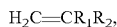

Perfluoro-2-methylene-4,5-dimethoxymethyl-1,3-
dioxolane
(Monomer G)

Perfluoro-2-methylene-1,3-dioxolane
(Monomer H)

Subsequent consideration and study of these materials has indicated that polymers incorporating even one perfluorodioxolane monomer may have special properties, including useful and stable fluid separation properties. In some cases, the perfluorodioxolane monomer has certain properties such that when polymerized as a homopolymer, the homopolymer has no substantial crystallinity to it. That is, the homopolymer of the perfluorodioxolane is amorphous.

An important feature of the present invention, is to balance the crystalline and amorphous phases of the copolymer material. If the copolymer is too crystalline or tightly packed, the membrane selective layer may have undesirably low permeability. Conversely, a looser, open or more flexible structure may result in a membrane with high fluxes, but poor selectivity. Therefore, the fluorovinyl monomer should be one that counterbalances the characteristics of the dioxolane monomer, In certain aspects, the fluorovinyl monomer is selected from known monomers, such as those described in Mikes et al, "Synthesis and Characterization of Perfluoro-3-methylene-2,4,-dioxabicyclo[3,3,0]octane: Homo-and Copolymerization with Fluorovinyl Monomers" J Polym Sci Part A: Polym Chem, 47: 6571-6578 (2009) or Teng, "Overview of the Development of the Fluoropolymer Industry," Appl. Sci, 2012; 2, 496-512, each incorporated herein by reference. These fluorovinyl monomers include, but are not limited to trifluoroethylene, tetrafluoroethylene (TFE), chlorotrifluoroethylene (CTFE) perfluoro methyl vinyl ether (PFMVE), perfluoroethyl vinyl ether (PFEVE), perfluoropropyl vinyl ether (PFPVE), vinyl fluoride (VF), vinylidene fluoride (VDF), and perfluoromethoxy vinyl ether (PFMOVE).

In some aspects, the fluorovinyl monomer is selected from a structure having one of the following formulas:

$$F_2C=CFR,$$

where R is H, Cl, a C1-C6 perfluoroalkyl, or OX, where X is a C1-C6 perfluoroalkyl or a C1-C12 perfluorooxyalkyl having one or more ether groups, or $$H_2C=CR_1R_2,$$

where $R_1$ is F, H, C1-C6 perfluoroalkyl, OX, or where X is a C1-C6 perfluoroalkyl or a C1-C12 perfluorooxyalkyl having one or more ether groups, and $R_2$ is F, C1-C6 perfluoroalkyl, or OX, or where X is a C1-C6 perfluoroalkyl or a C1-C12 perfluorooxyalkyl having one or more ether groups.

Depending on the specific properties of the dioxolane monomer that is used, and the comonomer with which it is polymerized, the resulting copolymer may have a glass transition temperature Tg(c) that is higher or lower than the glass transition temperature of a homopolymer, Tg(h), of the dioxolane monomer. For this effect to be of sufficient utility, Tg(c) is normally at least 5° C., preferably 10° C., lower or higher than the Tg(h).

We use the Flory-Fox equation to calculate the Tg(c) based on the Tg(h) of homopolymers of the two monomers. The equation is:

$$\frac{1}{T_g} = \frac{w_1}{T_{g,1}} + \frac{w_2}{T_{g,2}},$$

where $w_1$ and $w_2$ are weight fractions of components 1 and 2, respectively.

An important advantage of the present invention is that copolymerization of perfluorinated dioxolane monomers with a fluorovinyl monomer as described above can result in higher membrane selectivity for desired fluids than can be obtained using prior art membranes.

Due to their advantageous properties, the membranes and processes of the invention are useful for many fluid separation applications. Specific examples include, but are not limited to the separation of various non-fluorinated gases, for example, nitrogen, helium, carbon dioxide, and hydrogen from methane. Such separations are important in natural gas processing, for example.

The fluid mixture, may contain at least two components, designated component A and component B, that are to be separated from each other and optionally another component or components in the stream. The permeating component may be either a valuable fluid that is desired to retrieve as an enriched product, or a contaminant that is desired to remove. Thus, either the permeate stream or the residue stream, or both, may be the useful products of the process.

In certain aspects, the invention is a process for separating two components, A and B, of a fluid mixture wherein component A is hydrogen and component B is methane. Such a mixture may be found in a steam reforming process. For example, the process of the invention may be used to recover hydrogen from synthesis gas, to remove carbon dioxide from synthesis gas, or to adjust the ratio of hydrogen to carbon monoxide in synthesis gas.

In certain aspects, the invention is a process for separating two components, A and B, of a fluid mixture wherein component A is carbon dioxide and component B is methane. This process may be involved in carbon capture and storage or used in the separation of $CO_2$ from natural gas.

In other aspects, the invention is a process for separating two components, A and B, of a fluid mixture wherein component A is nitrogen and component B is methane. This process may be involved in removing nitrogen from nitrogen-contaminated natural gas.

In yet another aspect, the invention is a process for separating two components, A and B, of a fluid mixture wherein component A is helium and component B is methane. This process may be useful for producing helium through natural gas extraction and subsequent purification.

In other aspects, the invention is a process for separating two components, A and B, of a fluid mixture wherein component A is water and component B is either an alcohol, ketone, ether, or ester. In certain aspects, component B may be a solvent, such as ethanol, bioethanol, propanol, acetone and the like. This process may be useful in the dehydration of aqueous solvent mixtures.

In certain aspects, the invention is a process for separating two components, A and B, of a fluid mixture wherein component A is an unsaturated hydrocarbon compound and component B is a saturated hydrocarbon compound. Such fluid separation processes include, but are not limited to, olefin/paraffin separations, which may be useful in recovering unreacted olefins in petrochemical operations.

In a further aspect, the invention is a process for separating two components, A and B, of a fluid mixture Wherein component A is an aromatic hydrocarbon compound and component B is an aliphatic hydrocarbon compound. In another aspect, the invention is a process for separating two components, A and B, of a fluid mixture wherein component A is a first aromatic hydrocarbon compound and component B is a second aromatic hydrocarbon compound. Both of these processes may be useful, as a low-energy alternative to distillation in petrochemical and refinery, operations.

In other aspects, the invention is a process for separation two components, A and B, of a fluid mixture wherein component A is a linear hydrocarbon compound and component B is a branched hydrocarbon compound. This process may be useful in refinery operations to enhance the octane rating of gasoline, for example.

BRIEF DESCRIPTION OF THE DRAWINGS

None.

DETAILED DESCRIPTION OF THE INVENTION

The term "fluid" as used herein means a gas, vapor, or liquid.

The term "fluid separation" as used herein refers to molecular separations that can be carried out in three different modes: (1) gas separation (membrane is in contact with a gas or vapor phase on both sides of the membrane), (2) hydraulic permeation (membrane is in contact with a liquid or supercritical phase on both sides of the membrane), and (3) pervaporation (membrane is in contact with a liquid or supercritical phase on one side of the membrane and with a gas vapor phase on the other side of the membrane). The membrane materials described herein can be used in any one of the fluid separation modes.

The term "Polymer" as used herein generally includes, but is not limited to, homopolymers, copolymers, such as for example, block, graft, random and alternating copolymers; terpolymers, etc, and blends and modifications thereof. Furthermore, unless otherwise specifically limited, the term "polymer" shall include all possible geometrical configurations of the material. These configurations include, but are not limited to isotactic and atactic symmetries.

The term "copolymer" as used for simplicity herein refers to all polymers having at least two different monomer units, and thus includes, terpolymers and any other polymers having more than two different monomer units.

The terms "fully-fluorinated" and "perfluorinated" as used herein are interchangeable and refer to a compound where all of the available hydrogen bonded to carbon have been replaced by fluorine.

The term "membrane" as used herein refers to a thin selective layer supported on an integral or discrete support, such as an integral asymmetric membrane or a composite membrane. The membrane generally has a selective layer thickness of less than 10 μm, and more specifically less than 5 μm.

The invention relates to a process for separating two components, A and B, of a fluid mixture. The separation is carried out by running a stream of the fluid mixture across a membrane that is selective for the desired component to be separated from another component. The desired component to be separated into the permeate may be either Component A or Component. B, The process results, therefore, in a permeate stream enriched in the desired component and a residue stream depleted in that component.

At least the selective layer responsible for the fluid discriminating properties of the membrane is made from a glassy copolymer. The copolymer should be substantially amorphous, Crystalline polymers are typically difficult to dissolve, and thus render membrane making difficult. They also exhibit generally very low gas permeabilities. Crystalline polymers are not normally suitable for the selective layer, therefore.

The selective layer copolymer should be fluorinated, and generally the degree of fluorination should be high, to increase the chemical inertness and resistance of the material. By high, we mean having a fluorine carbon ratio of atoms in the polymer of at least 1:1, and more preferably greater than 1.5:1. Most preferably, the polymer is perfluorinated, even if the perfluorinated structure has less than a 1:1 fluorine:carbon ratio, Various materials may be used for the copolymeric selective layer to meet the characterizing requirements. These include copolymers comprising a dioxolane monomer and a fluorovinyl monomer.

The dioxolane monomers as described herein are characterized by a 1,3-dioxolane ring, having the general form:

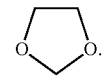

In some embodiments, preferred dioxolane monomers may be selected from perfluoro-2-methylene-1,3-dioxolane derivatives containing various substituent groups at the fourth and fifth positions of the dioxolane ring. These monomers are represented, for example, by the structures found in Monomers A-H of Table 1, above.

A homopolymer of perfluoro-2-methylene-1,3-dioxlane (Monomer H) is crystalline in nature, which was confirmed by Mikes et al., "Characterization and Properties of Semi-crystalline and Amorphous Perfluoropolymer: poly(perfluoro-2-methylene-1,3-dioxolane)." Polymers for Advanced Technologies, v. 22, pp, 1272-1277 (2011). This crystallinity reflects the ability of the repeat unit in the homopolymer of Monomer H to pack tightly forming ordered structures. As a result, a homopolymer of Monomer H does not dissolve in fluorinated solvents. However, as described herein, copolymerizing a perfluorinated dioxolane monomer with a fluorovinyl monomer, for example, in she appropriate amount may result in an overall amorphous structure, which is desirable for fluid separation membrane materials.

Thus, in some embodiments, the fluorovinyl monomer may be selected from the group consisting of trifluoroethylene, tetrafluoroethylene (TFE), chlorotrifluoroethylene (CTFE), perfluoro methyl vinyl ether (PFMVE), perfluoroethyl vinyl ether (PFEVE), perfluoropropyl vinyl ether (PFPVE), vinyl, fluoride (VF), vinylidene fluoride (VDF), and perfluoromethoxy vinyl ether (PFMOVE), Generally, dioxolanes can be prepared by actualization of aldehydes and ketalization of ketones with ethylene glycol. Formulations embracing those suitable for use in the invention are described in U.S. Pat. Nos. 3,308,107; 5,051,114: 7,754,901; 7,635,780; and 8,168,808 incorporated herein by reference. Copolymerization of the amorphous monomers in Table 1 with :a fluorovinyl monomer may be carried out in hulk or in solution using 0.1-1.0% of a free radical initiator, such as perfluorodibenzoylperoxide car tert-butyl peroxypivalate. The polymer obtained is purified by precipitating the solution with the addition of a non-solvent, such as dichloromethane. The isolated polymer is dried and the composition is determined by measuring NMR spectrum.

With the fluoropolymers described herein, the bonding of the monomers occurs outside the main dioxolane ring. This process is different than dioxole polymerization, which polymerize by the opening of a double bond within a five-member ring.

In certain embodiments, copolymerization of amorphous perfluorodioxolanes with a fluorovinyl monomer is represented by the following exemplary formula:

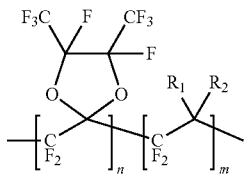

where $R_1$ is F, Cl, H, $OCF_3$, or $OC_3H_7$, and
$R_2$ is F,
and m and n are positive integers.

In certain embodiments, the copolymer may comprise more than one perfluorinated dioxolane monomer or more than one fluorovinyl monomer.

When any pair of monomers is used, one will tend to be more densely packed and perhaps crystalline than the other, and the respective proportions of the two monomers will alter the membrane properties. When copolymerized with the fluorovinyl monomers, the perfluorodioxolanes tend to frustrate polymer chain packing, yielding a selective layer with higher free volume and higher fluid permeability. The resulting copolymer is not as crystalline as a fluorovinyl monomer homopolymer and has a higher glass transition temperature. Thus, the copolymer has a glass transition temperature, Tg(c), that is higher, at least 5° C. higher, preferably at, least 10° C. higher, than a homopolymer made from the fluorovinyl monomer having a homopolymer glass transition temperature, Tg(h).

Within, the range of amorphous copolymers, there is a trade-off between permeance and selectivity. Relatively large proportions of the second monomer decrease permeance in favor of the selectivity, and relatively large proportions of the first dioxolane monomer decrease selectivity in favor of performance.

In a preferred embodiment, the copolymer is an ideal random copolymer.

The copolymer chosen for the selective layer can be used to form membranes by any convenient technique known in the art, and may take diverse forms. Because the polymers are glassy and rigid, an unsupported film, tube or fiber of the polymer may be usable in principle as a single layer membrane. However, such single-layer films will normally be too thick to yield acceptable transmembrane flux, and in practice, the separation membrane usually comprises a very thin selective layer that forms part of a thicker structure. This may be, for example, an integral asymmetric membrane, comprising a dense skin region that forms the selective layer and a microporous support region. Such membranes were originally developed by Loeb and Sourirajan, and their preparation in flat sheet or hollow fiber form is now conventional in the art and is described, for example, in U.S. Pat. No. 3,133,132 to Loeb, and U.S. Pat. No. 4,230,463 to Henis and Tripodi.

As a further, and a preferred, alternative, the membrane may he a composite membrane, that is, a membrane having multiple layers. Modern composite membranes typically comprise a highly permeable but relatively non-selective support membrane, which provides mechanical strength, coated with a thin selective layer of another material that is primarily responsible for the separation properties. Typically, but not necessarily, such a composite membrane is made by solution-casting the support membrane, then solution-coating the selective layer. General preparation techniques for making composite membranes of this type, are well known, and are described, for example, in U.S. Pat. No. 4,243,701 to Riley et al., incorporated herein by reference, Again, the membrane may take flat-sheet, tube or hollow-fiber form. The most preferred support membranes are those with an asymmetric structure, which provides a smooth, comparatively dense surface on which to coat the selective layer. Support membranes are themselves frequently east onto a backing web of paper or fabric. As an alternative to coating onto a support membrane, it is also possible to make a composite membrane by solution-casting the polymer directly onto a non-removable backing web, as mentioned above. In hollow-fiber form, multilayer composite membranes may be made by a coating procedure as taught, for example, in U.S. Pat. Nos, 4,863,761; 5,242,636; and 5,156,888, or by using a double-capillary spinneret of the type taught in U.S. Pat. Nos. 5,141,642 and 5,318,417.

A gutter layer may optionally be used between the support membrane and the selective layer, for example to smooth the support surface and channel fluid to the support membrane pores. In this case, the support membrane is first coated with the gutter layer, then with the perfluoro selective layer as described herein.

Multiple Selective Layers may also be used.

The thickness of a membrane, as used in the art, normally refers to the thickness of the selective layer or skin of the membrane. The thickness can be chosen according to the proposed use, but will generally be no thicker than 10 μm or 5 μm, and typically no thicker than 1 μm. It is preferred that the selective layer be sufficiently thin that the membrane provide a pressure-normalized hydrogen flux, as measured with pure hydrogen gas at 25'C, of at least about 100 GPU (where 1 GPU=1×10$^{-6}$ cm$^3$(STP)/cm$^2$·s·cmHg), more preferably at least about 200 GPU and most preferably at least about 400 GPU. In a preferred embodiment, the selective layer thickness is no greater than about 0.5 μm.

Once formed, the membranes exhibit a combination of good mechanical properties, thermal stability, and high chemical resistance. The fluorocarbon polymers that form the selective layer are typically insoluble except in perfluorinated solvents and arc resistant to acids, alkalis, oils, low-molecular-weight esters, ethers and ketones, aliphatic and aromatic hydrocarbons, and oxidizing agents, making them suitable for use not only in the presence of C$_{3+}$ hydrocarbons, but in many other hostile environments.

The membranes of the invention may be prepared in any known membrane form and housed in any convenient type of housing and separation unit. We prefer to prepare the membranes in flat-sheet form and to house them in spiral-wound modules. However, flat-sheet membranes may also be mounted in plate-and-frame modules or in any other way. If the membranes are prepared in the form of hollow fibers or tubes, they may be potted in cylindrical housings or otherwise, The membrane separation unit comprises one or more membrane modules. The number of membrane modules required will vary according to the volume of fluid to he treated, the composition of the feed fluid, the desired compositions of the permeate and residue streams, the operating pressure of the system, and the available membrane area per module. Systems may contain as few as one membrane module or as many as several hundred or more. The modules may he housed individually in pressure vessels or multiple elements may be mounted together in a sealed housing of appropriate diameter and length.

Of particular importance, the membranes and processes of the invention are useful in applications for producing hydrogen or chemicals from hydrocarbon feedstocks, such as reforming or gasification processes followed, by separation or chemical synthesis. Steam reforming is well known in the chemical processing arts, and involves the formation of various gas mixtures commonly known as synthesis gas or syngas from a light hydrocarbon feedstock, steam and optionally other gases, such as air, oxygen or nitrogen. Synthesis gas usually contains at least hydrogen, carbon dioxide, carbon monoxide and methane, hut the exact composition can he varied depending on its intended use.

Plant design and process operating conditions thus differ in their details, but the steam reforming process always includes a baste Steam, reforming reaction step, carried out at high temperature and elevated pressure, and one or more subsequent treatments of the raw synthesis gas to remove carbon dioxide or make other adjustments to the gas composition. The processes of the invention are expected to be especially useful in carrying out such treatments.

In another aspect, the invention is a process for separating carbon dioxide from methane, especially if the mixture also contains C$_{3+}$ hydrocarbon vapors. Such a mixture might he encountered during the processing of natural gas; of associated gas from oil wells, or of certain petrochemical streams, for example. The processes of the invention are expected to be useful as part of the gas treatment train, either in the field or at a gas processing plant, for example.

In another aspect, the invention is a process for recovering helium from natural gas. Helium is a rare gas on Earth. Almost all of the commercial helium requirements are supplied by extraction from helium-containing natural gas by low temperature fractional distillation processes. The resulting helium rich gases are further purified or refined using additional cryogenic distillation steps or by pressure swing adsorption (RSA) processes which selectively remove other gases. These final refining steps result in commercial grades of helium in excess of 99.9%. The processes of the invention are expected to be used in replacing or supplementing one ore more of the unit operations in the helium recovery plant.

In yet another aspect, the invention is a process for separating nitrogen from natural gas. The goal will often be to reduce the nitrogen content of the natural gas to no more than about 4% nitrogen, which is an acceptable total inserts value for pipeline gas. In other circumstances, a higher or lower nitrogen target value may be required. Once again, the processes of the invention are expected to be useful in field or plant equipment as standalone or supplementary units to meet the desired nitrogen concentration target.

Additionally, in another aspect, the invention is a process for separating oxygen, from nitrogen. Oxygen is used to enhance the combustion of all fuels, enabling improved burning zone control, and lowering emissions. The present invention is expected to yield enriched oxygen that can be used advantageously in combustion processes, such as kilns, or he u,sing low-grade fuels, where reduction in ballast nitrogen is beneficial. Advantageously, this separation may be also be useful for producing nitrogen, where the separated nitrogen can be used in applications where an inert, stable gas is, needed, such as in chemical and petrochemical plants, semiconductor manufacturing, vehicle tires, or fuel systems.

In a further aspect, the invention is a process for the dehydration of aqueous solvent mixtures. The aqueous solvent mixture may include an alcohol, such as ethanol, bioethanol produced from natural sources, and propanol., or other solvents, such as acetone and the like. A major drawback to more economical use o bioethanol as a fuel is the energy used to grow the feedstock, to ferment it, and to separate a dry ethanol product from the fermentation broth. The processes of the invention are expected to be useful in lowering the energy costs associated with ethanol purification (dehydration).

In other aspects, the invention is a process for separating unsaturated hydrocarbon compounds from saturated hydrocarbon compounds. This type of process typically occurs in petrochemical operations and includes separations such as olefins from paraffins, such as propylene from propane, n-butene or isobutene from n-butanol or isobutanol, and styrene from ethylbenzene.

In certain aspects, the invention is a process for separating an aromatic hydrocarbon compound from an aliphatic hydrocarbon compound. Examples of such separations include the separation of benzene, toluene and xylene from octane, heptane, methylcyclohexane, and cyclohexane. Benzene, toluene, and xylene are feedstocks for nine of the top 50 chemicals produced in the United States and are produced at a rate of about 36 million tons/year. Thus, an energy savings of even 1,000 Btu/kg would save about 36 trillion Btu/year.

In another aspect, the invention is a process for separating a first aromatic hydrocarbon compound from a second aromatic hydrocarbon compound. These separations include for example, benzenelethylbenzene, benzeneltoluene, and ethylbenzenelstyrene. Distillation of such mixtures consumes about 80 trillion Btu/year of energy in the United States. The processes of the present invention are expected to result in a potential savings of about 20-50 trillion Btu/year.

The invention can also be used in refinery operations to enhance the octane rating of the gasoline pool by separating linear compounds from branched compounds. For example, n-butane, n-pentane, n-hexane, and n-heptane may be separated from 2,3-dimethylbutanol, iso-octane, 2,2-dimethyl butanol, iso-pentane, and iso-butane.

The invention is now illustrated in further detail by specific examples. These examples are intended to further clarify the invention, and are not intended to limit the scope in any way,

EXAMPLES

Example 1

Membrane Preparation

Composite membranes were prepared using copolymer solutions prepared from the Monomers A-H found in Table 1 and copolymerized using the methods described herein.

Membranes were made using different fluorovinyls and different percentages of fluorovinyl monomers from about 20-55 mol %. The experiments established that copolymers and composite membranes having selective layers incorporating the copolymers can be made from the range of materials in Table 1.

The perfluoro selective layers were coated onto support membranes, either on a small coater or by hand coating, and the membranes were finished by oven drying. Samples of each finished composite membrane were then cut into 12.6 cm² stamps,

Example 2

Pure-Gas Testing of the Perfluoro Composite Membranes

A selection of the membranes from Example 1 was subjected to gas permeation tests. The membranes were tested in a permeation test-cell apparatus, with pure gases at room temperature and 50 psig feed pressure. The gas fluxes of the membranes were measured, and the permeances and selectivities were calculated.

For comparative purposes, tests were also run with membranes having selective layers made from several formulations of Hyflon® AD, Cytop®, and Teflon® AF, The results for representative copolymers having different proportions of fluorovinyl monomers are shown in Tables 2-4, below.

TABLE 2

Pure-Gas Selectivity Results

| Sample | Type and Percentage of Fluorovinyl Monomer | Pure-Gas Selectivity $H_2/CH_4$ | $CO_2/CH_4$ |
|---|---|---|---|
| Polymer 1 | 30 mol % CTFE | 200 | 50 |
| Polymer 2 | 55 mol % CTFE | 90 | 30 |
| Polymer 3 | 53 mol % PFPVE | 10 | 10 |
| Polymer 4 | 53 mol % 3,3,3-trifluoro-2-(trifluoromethyl)-1-propene | 6.0 | 7.0 |
| Polymer 5 | 23 mol % VDF | 80 | 30 |
| Hyflon® AD60 | 40 mol % TFE | 20 | 20 |
| Hyflon® AD40 | 60 mol % TFE | 40 | 20 |
| Cytop® |  | 50 | 30 |
| Teflon® AF2400 | 13 mol % TFE | 5.0 | 6.0 |

Example 3

Reproducibility Testing

TABLE 4

Pure-Gas Permeation Results for a Copolymer of 70 mol % D/30 mol % CTFE

| Stamps | Permeance (gpu) | | | Selectivity | | | | |
|---|---|---|---|---|---|---|---|---|
| | $H_2$ | He | $CO_2$ | $N_2/CH_4$ | $O_2/N_2$ | $H_2/CH_4$ | $He/CH_4$ | $CO_2/CH_4$ |
| 1 | 360 | 820 | 90 | 6.0 | 5.0 | 190 | 440 | 50 |
| 2 | 340 | 770 | 80 | 6.0 | 5.0 | 210 | 480 | 50 |
| 3 | 260 | 710 | 60 | 6.0 | | 200 | 540 | 50 |
| 4 | 300 | 760 | 70 | 5.0 | | 160 | 410 | 40 |
| Homopolymer of D | 1,800 | 2,530 | 1,070 | 3.0 | | 34 | 48 | 20 |
| Hyflon® AD60 | 1,700 | 2,600 | 1,300 | 2.0 | | 20 | 30 | 20 |
| Hyflon® AD40 | 450 | 1,120 | 270 | 3.0 | | 40 | 90 | 20 |
| Cytop® | 290 | 790 | 150 | 3.0 | | 50 | 130 | 30 |
| Teflon® AF2400 | 10,000 | 10,000 | 13,000 | 1.0 | | 5.0 | 5.0 | 6.0 |

Samples 1-4 were tested to check for reproducibility of performance data. The results for Samples 1-4 were also compared to data from a homopolymer of Monomer D.

Example 4

Reproducibility Testing

TABLE 5

Pure-Gas Permeation Results for a Copolymer of 45 mol % D/55 mol % CTFE

| Stamps | Permeance (gpu) | | | Selectivity | | | |
|---|---|---|---|---|---|---|---|
| | $H_2$ | He | $CO_2$ | $N_2/CH_4$ | $H_2/CH_4$ | $He/CH_4$ | $CO_2/CH_4$ |
| 1 | 210 | 520 | 70 | 3.0 | 80 | 200 | 30 |
| 2 | 230 | 590 | 90 | 3.0 | 60 | 160 | 20 |
| 3 | 160 | 410 | 50 | 3.0 | 90 | 240 | 30 |
| Homopolymer of D | 1,800 | 2,530 | 1,070 | 3.0 | 34 | 48 | 20 |
| Hyflon ® AD60 | 1,700 | 2,600 | 1,300 | 2.0 | 20 | 30 | 20 |
| Hyflon ® AD40 | 450 | 1,100 | 270 | 3.0 | 40 | 90 | 20 |
| Cytop ® | 290 | 790 | 150 | 3.0 | 50 | 130 | 30 |
| Teflon ® AF2400 | 10,000 | 10,000 | 13,000 | 1.0 | 5.0 | 5.0 | 6.0 |

Samples 1-3 were tested to check for reproducibility of performance data. The results for Samples 1-3 were also compared to data, from a homopolymer of Monomer D.

As can be seen from Tables 3-5, in most cases copolymers with CTFE have better selectivity performance for pure gas than Teflon®, Hyflon® or Cytop®.

Examples 2-4 provided above demonstrate that the membrane materials described herein are capable of performing gas separation. However, as discussed above, the membrane materials can also be used for hydraulic permeation and pervaporation.

We claim:

1. A process for separating two components, A and B, of a fluid mixture having a ratio (Rf) of A:B, comprising:
    (a) passing the fluid mixture across a separation membrane having a feed side and a permeate side, the separation membrane having a selective layer comprising a copolymer consisting of a perfluorinated dioxolane monomer and a fluorovinyl monomer selected from one of the following formulas:

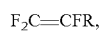

where R is H, Cl, a C1-C6 perfluoroalkyl, or OX, where X is a C1-C6 perfluoroalkyl or a C1-C12 perfluorooxyalkyl having one or more ether groups, or

where $R_1$ is F, H, C1-C6 perfluoroalkyl, or OX, or where X is a C1-C6 perfluoroalkyl or a C1-C12 perfluorooxyalkyl having one or more ether groups, and $R_2$ is F, C1-C6 perfluoroalkyl, or OX or where X is a C1-C6 perfluoroalkyl or a C1-C12 perfluorooxyalkyl having one or more ether groups,
    (b) providing a driving force for transmembrane permeation;
    (c) withdrawing from the permeate side a permeate stream having a ratio (Rp) of A:B, where Rp>Rf; and
    (d) withdrawing from the feed side a residue stream having a ratio (Rr) of A:B, where Rr<Rf.

2. The process of claim 1, wherein the fluorovinyl monomer is selected from the group consisting of trifluoroethylene, chlorotrifluoroethylene (CTFE), perfluoro methyl vinyl ether (PFMVE), perfluoroethyl vinyl ether (PFEVE), perfluoropropyl vinyl ether (PFPVE), vinyl fluoride (VF), vinylidene fluoride (VDF), and perfluoromethoxy vinyl ether (PFMOVE).

3. The process of claim 1, wherein the perfluofinated dioxolane monomer is selected from the group consisting of:

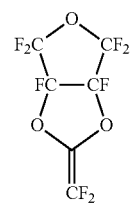

Perfluorotetrahydro-2-methylene-furo[3,4-d][1,3] dioxolane (Monomer A)

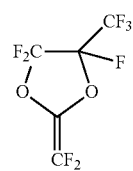

Perfluoro-2-methylene-4-methyl-1,3,-dioxolane (Monomer B)

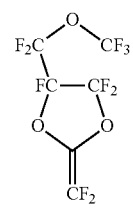

Perfluoro-2-methylene-4-methoxymethyl-1,3-dioxolane (Monomer C)

-continued

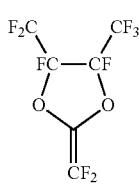

Perfluoro-2-methylene-4,5-dimethyl-1,3,-dioxolane (Monomer D)

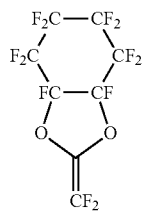

Perfluoro-3-methylene-2,4-dioxabicyclo[4,3,0]nonane (Monomer E)

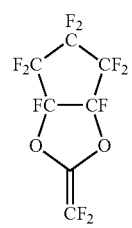

Perfluoro-3-methylene-2,4-dioxabicyclo-[3,3,0]octane (Monomer F)

-continued

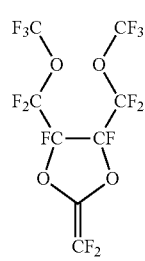

Perfluoro-2-methylene-4,5-dimethoxymethyl-1,3-dioxolane.

(Monomer G)

4. The process of claim 1, wherein component A is water and component B is an alcohol, ketone, ether, or ester.

5. The process of claim 1, wherein component A is an unsaturated hydrocarbon compound and component B is a saturated hydrocarbon compound.

6. The process of claim 5, wherein component A is an olefin and component B is a paraffin.

7. The process of claim 1, wherein component A is an aromatic hydrocarbon compound and component B is an aliphatic hydrocarbon compound.

8. The process of claim 1, wherein component A is a first aromatic compound and component B is a second aromatic compound.

9. The process of claim 1, wherein component A is a linear hydrocarbon compound and component B is a branched hydrocarbon compound.

10. The process of claim 1, wherein the separation membrane has a selective layer of thickness less than 10 μm.

* * * * *